(12) United States Patent
Juul-Mortensen et al.

(10) Patent No.: US 8,614,181 B2
(45) Date of Patent: Dec. 24, 2013

(54) STABILIZED PHARMACEUTICAL PEPTIDE COMPOSITIONS

(75) Inventors: Claus Juul-Mortensen, København V (DK); Dorte Kot Engelund, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 340 days.

(21) Appl. No.: 12/612,888

(22) Filed: Nov. 5, 2009

(65) Prior Publication Data

US 2010/0056451 A1 Mar. 4, 2010

Related U.S. Application Data

(60) Division of application No. 11/290,634, filed on Nov. 30, 2005, now Pat. No. 7,632,806, which is a continuation of application No. PCT/DK2004/000380, filed on Jun. 3, 2004.

(60) Provisional application No. 60/538,525, filed on Jan. 22, 2004, provisional application No. 60/476,279, filed on Jun. 5, 2003.

(30) Foreign Application Priority Data

Jun. 3, 2003 (DK) ................................. 2003 00819
Jan. 19, 2004 (DK) ................................. 2004 00075

(51) Int. Cl.
*A61K 38/26* (2006.01)

(52) U.S. Cl.
USPC .......................................... 514/7.2; 530/308

(58) Field of Classification Search
USPC .......................................... 514/7.2; 530/308
See application file for complete search history.

(56) References Cited

U.S. PATENT DOCUMENTS

| | | | |
|---|---|---|---|
| 4,468,346 A | 8/1984 | Paul et al. | |
| 5,206,219 A | 4/1993 | Desai | |
| 5,272,135 A | 12/1993 | Takruri | |
| 5,455,331 A | 10/1995 | Pearce | |
| 5,652,216 A | 7/1997 | Kornfelt et al. | |
| 5,705,483 A | 1/1998 | Galloway et al. | |
| 6,133,229 A | 10/2000 | Gibson et al. | |
| 6,184,201 B1 | 2/2001 | Drucker et al. | |
| 6,268,343 B1* | 7/2001 | Knudsen et al. | 514/4.8 |
| 6,274,553 B1 | 8/2001 | Furuya et al. | |
| 6,284,727 B1 | 9/2001 | Kim et al. | |
| 6,380,357 B2 | 4/2002 | Hermeling et al. | |
| 6,384,016 B1* | 5/2002 | Kaarsholm | 514/11.7 |
| 6,444,788 B1 | 9/2002 | Staby | |
| 6,569,832 B1* | 5/2003 | Knudsen et al. | 514/11.7 |
| 6,586,399 B1 | 7/2003 | Drucker et al. | |
| 6,844,321 B2 | 1/2005 | Arentsen | |
| 7,022,674 B2* | 4/2006 | DeFelippis et al. | 514/5.9 |
| 7,049,284 B2 | 5/2006 | Drucker et al. | |
| 7,056,886 B2 | 6/2006 | Isaacs | |
| 7,112,567 B2 | 9/2006 | Bridon et al. | |
| 7,226,990 B2* | 6/2007 | Knudsen et al. | 530/308 |
| 7,238,663 B2 | 7/2007 | DeFelippis et al. | |
| 7,273,921 B2* | 9/2007 | Dunweber et al. | 530/345 |
| 2001/0014666 A1 | 8/2001 | Hermeling et al. | |
| 2002/0151467 A1 | 10/2002 | Leung | |
| 2003/0060412 A1 | 3/2003 | Prouty, Jr. et al. | |
| 2003/0069182 A1 | 4/2003 | Rinella, Jr. | |
| 2003/0119734 A1 | 6/2003 | Flink et al. | |
| 2003/0207802 A1 | 11/2003 | DeFelippis et al. | |
| 2003/0220243 A1 | 11/2003 | Glaesner et al. | |
| 2003/0220255 A1 | 11/2003 | Knudsen et al. | |
| 2006/0084605 A1 | 4/2006 | Engelund et al. | |
| 2006/0287221 A1 | 12/2006 | Knudsen et al. | |

FOREIGN PATENT DOCUMENTS

| | | |
|---|---|---|
| EP | 0431679 | 11/1990 |
| EP | 0438767 | 12/1990 |
| EP | 699687 | 8/1995 |
| EP | 0708179 | 4/1996 |
| EP | 747390 | 12/1996 |
| EP | 0926159 | 6/1999 |
| EP | 1329462 | 10/2001 |
| EP | 1424077 | 5/2002 |
| EP | 1344533 | 9/2003 |
| EP | 1396499 | 3/2004 |
| JP | 2002-524514 | 8/2002 |
| WO | WO9000200 | 1/1990 |
| WO | WO9219260 | 11/1992 |
| WO | WO9323010 | 11/1993 |
| WO | WO9522560 | 2/1995 |
| WO | WO9510605 | 4/1995 |
| WO | WO9513825 | 5/1995 |
| WO | WO9620005 | 7/1996 |
| WO | WO9638469 | 12/1996 |
| WO | WO9808871 | 3/1998 |

(Continued)

OTHER PUBLICATIONS

Malendowicz, L.K. et al., "Preproglucagon derived peptides and thyrotropin (TSH) secretion in the rat: Robust and sustained lowering of blood TSH levels in extendin-4 injected animals", International Journal of Molecular Medicine, vol. 10, pp. 327-331 (2002).

Bailey et al. The Kinetics of Enzyme-Catalysed Reactions Biochemical Engineering Fundamentals, $2^{nd}$ Ed., pp. 129-148 (1986).

Chou, J. Z. et al., Journal of Pharmaceutical Sciences, A Radioimmunoassay for LY315902, An Analog of Glucagon-Like Insulinotropic Pepride, and Its Application in the Study of Canine Pharmacokinetics, vol. 86(7), pp. 768-773 (1997).

D. Voet and J.G. Voet, Biochem, $2^{nd}$ Ed., pp. 235-241 (1995).

D.E. Smilek et al., Proc Natl Acad Sci USA, vol. 88, pp. 9633-9637, (1991).

Entry for Glycerin in Drugs.Com (www.drugs.com/ppa/glycerin-glycerol.html), Printed Aug. 4, 2009.

European Pharmacopoeia, 2007, vol. 1, p. 730, Council of Europe-Strasbourg.

(Continued)

*Primary Examiner* — David Lukton

(74) *Attorney, Agent, or Firm* — Rosemarie R. Wilk-Orescan

(57) ABSTRACT

Method for increasing the shelf-life of a pharmaceutical composition for parenteral administration comprising a glucagon-like peptide which is prepared from a peptide product that has been subjected to treatment at a pH above neutral pH.

12 Claims, No Drawings

(56) References Cited

FOREIGN PATENT DOCUMENTS

| WO | WO9916417 | 4/1999 |
| WO | WO9921889 | 5/1999 |
| WO | WO 99/29336 | 6/1999 |
| WO | WO 99/30731 | 6/1999 |
| WO | WO9943341 | 9/1999 |
| WO | WO9943706 | 9/1999 |
| WO | WO9943707 | 9/1999 |
| WO | WO 00/37098 | 12/1999 |
| WO | WO 00/15224 | 3/2000 |
| WO | WO0041546 | 7/2000 |
| WO | WO0055119 | 9/2000 |
| WO | WO0100223 | 1/2001 |
| WO | WO0143762 | 6/2001 |
| WO | WO 01/49314 | 7/2001 |
| WO | WO0152937 | 7/2001 |
| WO | WO0155213 | 8/2001 |
| WO | WO0177141 | 10/2001 |
| WO | WO0267989 | 1/2002 |
| WO | WO 02/47715 | 6/2002 |
| WO | WO 02/48183 | 6/2002 |
| WO | WO 03/002136 | 1/2003 |
| WO | WO03013589 | 2/2003 |
| WO | WO 03/020201 | 3/2003 |
| WO | WO03035099 | 5/2003 |
| WO | WO2004029076 | 4/2004 |
| WO | WO2004105781 | 12/2004 |
| WO | WO2005000222 | 1/2005 |
| WO | WO2005/046716 | 5/2005 |
| WO | WO2006025882 | 3/2006 |

OTHER PUBLICATIONS

G.F. Stamper et al., "Accelerated Stability Testing of Proteins and Peptides: Ph-Stability Profile of Insulinotropin Using Traditional Arrheneius and Non-Linear Fitting Analysis", Drug Development and Industrial Pharmacy, 1995, vol. 21, No. 13, pp. 1503-1511.

H. Qi et al., "Stability and Stabilization of Insulinotropin in a Dextran Formulation", PDA Journal of Pharmaceutical Science & Technology, vol. 49, No. 6, Nov.-Dec. 1995, pp. 289-293.

H.J.C. Berendsen, A Glimpse of the Holy Grail, Science, vol. 282, pp. 642-643 (1998).

Larsen, P.J. et al., Systemic Administration of the Logn Acting GLP-1, Diabetes, vol. 50, 2530-9,2000.

N. Good et al., "Hydrogen Ion Buffers for Biological Research", Biochemistry, 1966, vol. 5, No. 2, pp. 467-477.

Rudinger, In: Peptide Hormones, JA Parsons, Ed., pp. 1-7 (1976).

S.E. Bondos & A. Bicknell, Detection and Prevention of Protein Aggregation Before During and After Purification, Analytical Biochemistry, 2003, 223-231, vol. 316, Academic Press.

Senderoff, R.I. et al, Consideration of Conformational Transitions and Racemization During Process Development of Recombinant Glucagon-Like Peptide-1, Journal of Pharmaceutical Sciences, 1998, 183-189, vol. 87—No. 2, American Ciiemical Society & American Piirm. Assc.

SIGMA, http://www.sigma-genosys.com/peptide design.asp (Accessed Dec. 16, 2004).

Singh, S. et al. AAPS Pharmscitech, vol. 4(3), pp. 334-342 (2003).

Skovgaard et al., "Using Evolutionary Information and Ancestral Sequences to Understand the Sequence-Function Relationship in GLP-1 Agonists," J. Mol. Bio., 2006, vol. 363, pp. 977-988.

Tsoka et al, Selective Flocculation ands Precipitation for the Improvement of Virus-Like Particle Recovery From Yeast Homogenate, Biotechnol Prog. vol. 16(4), pp. 661-667 (2000).

Non-Final Office Action Dated Dec. 9, 2009 in U.S. Appl. No. 12/184,531, filed Aug. 1, 2008 by Juul-Mortensen.

Non-Final Office Action in U.S. Appl. No. 10/185,923, filed Jun. 27, 2002, Inventors: Funk et al. Sent Mar. 10, 2006.

Non-Final Office Action in U.S. Appl. No. 10/185,923, filed Jun. 27, 2002, Inventors: Flink et al. Sent Oct. 9, 2007.

Non-Final Office Action in U.S. Appl. No. 10/719,601, filed Nov. 21, 2003, Inventors: Markussen et al. Sent Mar. 4, 2005.

Non-Final Office Action in U.S. Appl. No. 11/220,266, filed Sep. 6, 2005, Inventors: Markussen et al. Sent Sep. 14, 2006.

Non-Final Office Action in U.S. Appl. No. 11/220,266, filed Sep. 6, 2005, Inventors: Markussen et al. Sent Feb. 11, 2008.

Non-Final Office Action in U.S. Appl. No. 11/220,266, filed Sep. 6, 2005, Inventors: Markussen et al. Sent Oct. 1, 2007.

Non-Final Office Action in U.S. Appl. No. 11/290,635, filed Nov. 30, 2005, Inventors: Juul-Mortensen et al. Sent Feb. 2, 2007.

Non-Final Office Action in U.S. Appl. No. 11/365,274, filed Mar. 1, 2006, Inventors: Schlein et al. Sent Aug. 20, 2007.

Non-Final Office Action in U.S. Appl. No. 11/365,274, filed Mar. 1, 2006, Inventors: Schlein et al. Sent Feb. 5, 2007.

Non-Final Office Action in U.S. Appl. No. 11/365,274, filed Mar. 1, 2006, Inventors: Schlein et al. Sent Jan. 28, 2009.

Non-Final Office Action in U.S. Appl. No. 11/435,977, filed May 17, 2006, Inventors: Pedersen et al. Sent Dec. 2, 2008.

Non-Final Office Action in U.S. Appl. No. 11/661,521, filed Feb. 27, 2007, Inventors: Christiansen et al. Sent Dec. 10, 2009.

Non-Final Office Action in U.S. Appl. No. 11/786,095, filed Apr. 11, 2007, Inventors: Flink et al. Sent Feb. 24, 2009.

Non-Final Office Action in U.S. Appl. No. 12/343,722, filed Dec. 24, 2008, Inventors: Flink et al. Sent May 22, 2009.

Final Office Action in U.S. Appl. No. 10/185,923, filed Jun. 27, 2002, Inventors: Flink et al. Sent Dec. 12, 2006.

Final Office Action in U.S. Appl. No. 10/185,923, filed Jun. 27, 2002, Inventors: Flink et al. Sent Jun. 14, 2005.

Final Office Action in U.S. Appl. No. 10/185,923, filed Jun. 27, 2002, Inventors: Flink et al. Sent Jun. 30, 2008.

Final Office Action in U.S. Appl. No. 11/290,635, filed Nov. 30, 2005, Inventors: Juul-Mortensen Sent Sep. 5, 2007.

Final Office Action in U.S. Appl. No. 11/365,274, filed Mar. 1, 2006, Inventors: Schlein et al. Sent Apr. 4, 2008.

Final Office Action in U.S. Appl. No. 11/365,274, filed Mar. 1, 2006, Inventors: Schlein et al. Sent Aug. 12, 2009.

Final Office Action in U.S. Appl. No. 11/435,977, filed May 17, 2006, Inventors: Pedersen et al. Sent Jun. 25, 2009.

Final Office Action in U.S. Appl. No. 11/786,095, filed Apr. 11,2007, Inventors: Flink et al. Sent Nov. 24, 2009.

Final Office Action in U.S. Appl. No. 12/343,722, filed Dec. 24, 2008, Inventors: Flink et al. Sent Feb. 18, 2009.

Brittain, Harry G., Buffers, Buffering Agents, and Ionic Equilibria, Encyclopedia of Pharmaceutical Technology, p. 385, 2007.

* cited by examiner

SEQUENCE LISTING

```
<160> NUMBER OF SEQ ID NOS: 6

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 31
<212> TYPE: PRT
<213> ORGANISM: Homo sapiens

<400> SEQUENCE: 2
```

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 33
<212> TYPE: PRT
<213> ORGANISM: Homo sapiens

<400> SEQUENCE: 3

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 4
<211> LENGTH: 39
<212> TYPE: PRT
<213> ORGANISM: Homo sapiens

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Homo sapiens

<400> SEQUENCE: 5

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 6
<211> LENGTH: 37
<212> TYPE: PRT
<213> ORGANISM: Homo sapiens

<400> SEQUENCE: 6

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Thr Lys Arg Asn
            20                  25                  30

Lys Asn Asn Ile Ala
        35
```

STABILIZED PHARMACEUTICAL PEPTIDE COMPOSITIONS

CROSS-REFERENCE TO RELATED PATENT APPLICATIONS

This patent application is a divisional of U.S. application Ser. No. 11/290,634, filed Nov. 30, 2005, now U.S. Pat. No. 7,632,806, which is a continuation (filed under 35 USC §120) of International Patent Application PCT/DK2004/000380 (published as WO 2004/105781), filed Jun. 3, 2004, which designated the US, and further claims the benefit of priority to U.S. Provisional Patent Application 60/538,525 filed Jan. 22, 2004 and U.S. Provisional Patent Application 60/476,279, filed Jun. 5, 2003; Danish Patent Application PA 2004 00075, filed Jan. 19, 2004; and Danish Patent Application PA 2003 00819, filed Jun. 3, 2003, the entirety of each of which is hereby incorporated by reference.

FIELD OF THE INVENTION

The present invention relates to the field of pharmaceutical compositions. More specifically the invention pertains to methods for preparing stable pharmaceutical compositions which are prepared from a bulk peptide product that has been subjected to treatment at pH above neutral pH.

BACKGROUND OF THE INVENTION

Therapeutic peptides are widely used in medical practise. Pharmaceutical compositions of such therapeutic peptides are required to have a shelf life of several years in order to be suitable for common use. However, peptide compositions are inherently unstable due to sensitivity towards chemical and physical degradation. Chemical degradation involves change of covalent bonds, such as oxidation, hydrolysis, racemization or crosslinking. Physical degradation involves conformational changes relative to the native structure of the peptide, i.e. secondary and tertiary structure, such as aggregation, precipitation or adsorption to surfaces.

Glucagon has been used for decades in medical practise within diabetes and several glucagon-like peptides are being developed for various therapeutic indications. The preproglucagon gene encodes glucagon as well as glucagon-like peptide 1 (GLP-1) and glucagon-like peptide 2 (GLP-2). GLP-1 analogs and derivatives as well as the homologous lizard peptide, exendin-4, are being developed for the treatment of hyperglycemia within type 2 diabetes. GLP-2 are potentially useful in the treatment of gastrointestinal diseases. However, all these peptides encompassing 29-39 amino acids have a high degree of homology and they share a number of properties, notably their tendency to aggregate and formation of insoluble fibrils. This property seems to encompass a transition from a predominant alpha-helix conformation to beta-sheets (Blundell T.L. (1983) The conformation of glucagon. In: Lefébvre P. J. (Ed) Glucagon I. Springer Verlag, pp 37-55, Senderoff R. I. et al., J. Pharm. Sci. 87 (1998)183-189, WO 01/55213). Aggregation of the glucagon-like peptides are mainly seen when solutions of the peptides are stirred or shaken, at the interface between solution and gas phase (air), and at contact with hydrophobic surfaces such as Teflon®.

Thus, various excipients must often be added to pharmaceutical compositions of the glucagon-like peptides in order to improve their stability. Shelf life of liquid parenteral formulations of these peptides must be at least a year, preferably longer. The in-use period where the product may be transported and shaken daily at ambient temperature preferably should be several weeks. Thus, there is a need for pharmaceutical compositions of glucagon-like peptides which have improved stability.

SUMMARY OF THE INVENTION

The present invention relates to the unexpected finding that bulk peptide products which have been treated at a pH above 8.0 increased the stability of the pharmaceutical compositions prepared from these bulk peptide products.

The present invention therefore relates to methods for increasing the shelf-life of a pharmaceutical composition for parenteral administration comprising a glucagon-like peptide which is prepared from a glucagon-like peptide product that has been subjected to treatment at a pH above neutral pH, to pharmaceutical compositions produced by such methods and to the use of such compositions in methods of treatment.

Definitions

The following is a detailed definition of the terms used in the specification.

The term "effective amount" as used herein means a dosage which is sufficient to be effective for the treatment of the patient compared with no treatment.

The term "reconstituted" as used herein referring to a pharmaceutical composition means an aqueous composition which has been formed by the addition of water or an appropriate aqueous solution to a solid material comprising the active pharmaceutical ingredient. Pharmaceutical compositions for reconstitution are applied where a liquid composition with acceptable shelf-life cannot be produced. An example of a reconstituted pharmaceutical composition is the solution which results when adding water or an appropriate aqueous solution to a freeze dried composition. The solution is often for parenteral administration and thus water for injection or any other appropriate solvent are used for reconstituting the solid material.

The term "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The term "glucagon-like peptide" as used herein refers to the homologous peptides derived from the preproglucagon gene, exendins and analogues and derivatives thereof. The peptides derived from the preproglucagon gene is glucagon, glucagon-like peptide 1 (GLP-1), glucagon-like peptide 2 (GLP-2) and oxynthomodulin (OXM). The exendins which are found in the Gila monster are homologous to GLP-1 and also exert an insulinotropic effect. Examples of exendins are exendin-4 and exendin-3.

The glucagon-like peptides have the following sequences

```
             1    5    10   15   20   25   30   35
Glucagon  HSQGT FTSDY SKYLD SRRAQ DFVQW LMNT-NH2

GLP-1     HAEGT FTSDV SSYLE GQAAK EFIAW LVKGR G
```

```
GLP-2      HADGS FSDEM NTILD NLAAR DFINW LIQTK ITD

Exen-      HGEGT FTSDL SKQME EEAVR LFIEW LKNGG PSSGA PPPS-NH2
din-4

Exen-      HSDGT FTSDL SKQME EEAVR LFIEW LKNGG PSSGA PPPS-NH2
din-3

OXM        HSQGT FTSDY SKYLD SRRAQ DFVQW LMDTK RNKNN IA
```

The term "analogue" as used herein referring to a peptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. Two different and simple systems are often used to describe analogues: For example $Arg^{34}$-GLP-1(7-37) or K34R-GLP-1(7-37) designates a GLP-1 analogue wherein amino acid residues at position 1-6 have been deleted, and the naturally occurring lysine at position 34 has been substituted with arginine (standard single letter abbreviation for amino acids used according to IUPAC-IUB nomenclature).

The term "derivative" as used herein in relation to a parent peptide means a chemically modified parent protein or an analogue thereof, wherein at least one substituent is not present in the parent protein or an analogue thereof, i.e. a parent protein which has been covalently modified. Typical modifications are amides, carbohydrates, alkyl groups, acyl groups, esters, pegylations and the like. An examples of a derivative of GLP-1(7-37) is $Arg^{34}$, $Lys^{26}(N^{\epsilon}$-($\gamma$-Glu($N^{\alpha}$-hexadecanoyl)))-GLP-1(7-37).

The term "GLP-1 peptide" as used herein means GLP-1(7-37), a GLP-1 analogue, a GLP-1 derivative or a derivative of a GLP-1 analogue.

The term "GLP-2 peptide" as used herein means GLP-2(1-33), a GLP-2 analogue, a GLP-2 derivative or a derivative of a GLP-2 analogue.

The term "exendin-4 peptide" as used herein means exendin-4(1-39), an exendin-4 analogue, an exendin-4 derivative or a derivative of an exendin-4 analogue.

The term "stable exendin-4 compound" as used herein means a chemically modified exendin-4(1-39), i.e. an analogue or a derivative which exhibits an in vivo plasma elimination half-life of at least 10 hours in man, as determined by the following method. The method for determination of plasma elimination half-life of an exendin-4 compound in man is: The compound is dissolved in an isotonic buffer, pH 7.4, PBS or any other suitable buffer. The dose is injected peripherally, preferably in the abdominal or upper thigh. Blood samples for determination of active compound are taken at frequent intervals, and for a sufficient duration to cover the terminal elimination part (e.g. Pre-dose, 1, 2, 3, 4, 5, 6, 7, 8, 10, 12, 24 (day 2), 36 (day 2), 48 (day 3), 60 (day 3), 72 (day 4) and 84 (day 4) hours post dose). Determination of the concentration of active compound is performed as described in Wilken et al., Diabetologia 43(51):A143, 2000. Derived pharmacokinetic parameters are calculated from the concentration-time data for each individual subject by use of non-compartmental methods, using the commercially available software WinNonlin Version 2.1 (Pharsight, Cary, N.C., USA). The terminal elimination rate constant is estimated by log-linear regression on the terminal log-linear part of the concentration-time curve, and used for calculating the elimination half-life.

The term "DPP-IV protected exendin-4 compound" as used herein means an exendin-4 compound which has been chemically modified to render said compound resistant to the plasma peptidase dipeptidyl aminopeptidase-4 (DPP-IV).

The term "immunomodulated exendin-4 compound" as used herein means an exendin-4 compound which is an analogue or a derivative of exendin-4(1-39) having a reduced immune response in humans as compared to exendin-4(1-39). The method for assessing the immune response is to measure the concentration of antibodies reactive to the exendin-4 compound after 4 weeks of treatment of the patient.

The term "bulk product" or "bulk peptide product" as used herein means the purified peptide product which is to be used for the manufacture of a pharmaceutical composition. Thus, the bulk product is normally obtained as the product from the final purification, drying or conditioning step. The bulk product may be crystals, precipitate, solution or suspension. The bulk product is also known in the art as the drug substance.

The term "isoelectric point" as used herein means the pH value where the overall net charge of a macromolecule such as a peptide is zero. In peptides there may be many charged groups, and at the isoelectric point the sum of all these charges is zero, i.e. the number of negative charges balances the number of positive charges. At a pH above the isoelectric point the overall net charge of the peptide will be negative, whereas at pH values below the isoelectric point the overall net charge of the peptide will be positive. The isoelectric point of a peptide may be determined by isoelectric focusing or it may be estimated from the sequence of the peptide by computational algorithms known in the art.

DESCRIPTION OF THE INVENTION

In one aspect the present invention relates to a method for increasing the shelf-life of a pharmaceutical composition which comprises a glucagon-like peptide, a pharmaceutically acceptable buffer and a pharmaceutically acceptable preservative, characterized in that said pharmaceutical composition is prepared from a bulk peptide product which has been subjected to treatment at a pH in the range from 8.1 to 9.6.

In another aspect the present invention relates to a method for increasing the shelf-life of a pharmaceutical composition which comprises a glucagon-like peptide and a pharmaceutically acceptable preservative, characterized in that said pharmaceutical composition is prepared from a bulk peptide which has been subjected to treatment at a pH in the range from 8.1 to 9.6. In another aspect the present invention relates to a method for increasing the shelf-life of a pharmaceutical composition which comprises a peptide, a pharmaceutically acceptable buffer and a pharmaceutically acceptable preservative, characterized in that said pharmaceutical composition is prepared from a bulk peptide product which has been subjected to treatment at a pH in the range from 8.1 to 9.6.

In another aspect the present invention relates to a method for increasing the shelf-life of a pharmaceutical composition which comprises a peptide and a pharmaceutically acceptable preservative, characterized in that said pharmaceutical composition is prepared from a bulk peptide which has been subjected to treatment at a pH in the range from 8.1 to 9.6.

In another aspect the present invention relates to a method for increasing the shelf-life of a pharmaceutical composition which comprises a glucagon-like peptide, a pharmaceutically acceptable buffer and a pharmaceutically acceptable preservative, characterized in that said pharmaceutical composition is prepared from a bulk peptide product which has been subjected to treatment at a pH in the range from 8.5 to 9.6.

In one aspect the present invention relates to a method for increasing the shelf-life of a pharmaceutical composition which comprises a glucagon-like peptide, a pharmaceutically acceptable buffer and a pharmaceutically acceptable preservative, characterized in that said pharmaceutical composition is prepared from a bulk peptide product which has been subjected to treatment at a pH in the range from 9.0 to 9.6.

In one aspect the present invention relates to a method for increasing the shelf-life of a pharmaceutical composition which comprises a glucagon-like peptide, a pharmaceutically acceptable buffer and a pharmaceutically acceptable preservative, characterized in that said pharmaceutical composition is prepared from a bulk peptide product which has been subjected to treatment at a pH in the range from 8.1 to 11.5.

In one embodiment the bulk peptide product has been subjected to a pH in the range from 8.1 to 10.0.

In another embodiment the bulk peptide product has been subjected to a pH in the range from 8.5 to 11.5.

In another embodiment the bulk peptide product has been subjected to a pH in the range from 8.5 to 10.0.

In another embodiment of the invention the bulk peptide product has been subjected to treatment at a pH in the specified range for a period from about 1 minute to about 12 hours, and at a temperature higher than the nucleation temperature (either as heterogeneous or homogeneous nucleation) of the bulk peptide to about 25° C.

In another embodiment of the invention the bulk peptide product has been subjected to treatment at a pH in the specified range for a period from 1 minute to 30 minutes, and at a temperature from about 5° C. to about 25° C.

It is to be understood that the invention may be realised through various combinations of pH values, temperature and time. These three variables may be combined within the above mentioned ranges. However, whereas one or two of the variables may suitably be chosen at the high end of the ranges, the remaining one or two variables are typically lower. For instance, if a high pH value such as pH 10 is used it is preferably combined with a lower temperature such as about 5-10° C. and/or a short time such as less than about 1 minute to about 6 hours. Useful combinations of variables are: pH 10.0 at 5° C. for about 3 hours, pH 10.0 at 15° C. for about 1 hour, or pH 11.0 at 5° C. for about 1 hours.

The growth of ice crystals, whether as a single crystal or as a polycrystal, is the initial nucleation process, only ice is produced with the freezing of water or a aqueous solution at low pressures, both on slow and rapid freezing. The nucleation of solutions may take place in two ways, depending on the concentration of the solute and the temperature. If a saturated solution is cooled, then it may become not only supercooled with respect to the ice phase, but also supersaturated with respect to the solute. In absence of appropriate freezing nuclei, the solution may supercool. Thus the temperature used during the treatment of the peptide at higher pH is to be kept above the nucleation temperature of the peptide at the prevailing conditions. The nucleation temperature is known to the person skilled in the art, and it may routinely be determined for the relevant peptide by experiments at different temperatures.

In one embodiment the pharmaceutical composition is a solution.

In another embodiment the pharmaceutical composition is a suspension.

In another embodiment the pharmaceutical composition is a solid, e.g. a freeze-dried formulation whereto the physician or the patient adds the solvent prior to use. The solvent used for reconstitution may be water for injection or another suitable solvent.

In another embodiment the bulk peptide product is prepared by freeze drying a solution or suspension of said glucagon-like peptide at said pH.

In another embodiment the bulk peptide product is treated at said pH during the manufacture of said pharmaceutical composition.

In another embodiment the bulk peptide product is treated at said pH after the final purification step in the manufacturing process.

In another embodiment the bulk peptide product is treated at said pH before being mixed with said pharmaceutically acceptable buffer.

In another embodiment the pH of the pharmaceutical composition is lower than the pH at which the solution or suspension of the bulk peptide is treated.

In another embodiment the pH of the pharmaceutical composition is at least 0.8 pH units lower than the pH at which the solution or suspension of the bulk peptide is treated.

In another embodiment the pH of said pharmaceutical composition is at least 1.5 pH units lower than the pH at which the solution or suspension of the bulk peptide is treated.

Pharmaceutical compositions comprising a glucagon-like peptide according to the present invention may be administered parenterally to patients in need of such treatment. Parenteral administration may be performed by subcutaneous injection, intramuscular injection, or intravenous injection by means of a syringe, optionally a pen-like syringe. Alternative administration can be performed by infusion, e.g. by use of an infusion pump.

In one embodiment the pH of said pharmaceutical composition or a reconstituted solution of said pharmaceutical composition is from pH 7.0 to pH 8.0, preferably from pH 7.2 to pH 7.8. In another embodiment the pH of said pharmaceutical composition or a reconstituted solution of said pharmaceutical composition is from pH 7.2 to pH 7.6. In another embodiment the pH of said pharmaceutical composition or a reconstituted solution of said pharmaceutical composition is from pH 7.4 to pH 7.8.

In another embodiment the isoelectric point of said glucagon-like peptide is from 3.0 to 7.0, preferably from 4.0 to 6.0.

In one embodiment said glucagon-like peptide is glucagon, a glucagon analogue or a derivative thereof.

In another embodiment said glucagon-like peptide is oxynthomodulin.

In one embodiment said glucagon-like peptide is GLP-1, a GLP-1 analogue, a derivative of GLP-1 or a derivative of a GLP-1 analogue.

In another embodiment said GLP-1 analogue is selected from the group consisting of $Gly^8$-GLP-1(7-36)-amide, $Gly^8$-GLP-1(7-37), $Val^8$-GLP-1(7-36)-amide, $Val^8$-GLP-1(7-37), $Val^8Asp^{22}$-GLP-1(7-36)-amide, $Val^8Asp^{22}$-GLP-1(7-37), $Val^8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), Val⁸His²²-GLP-1(7-36)-amide, Val⁸His²²-GLP-1(7-37), Val⁸Trp¹⁹Glu²²-GLP-1(7-37), Val⁸Glu²²Val²⁵-GLP-1(7-37), Val⁸Tyr¹⁶Glu²²-GLP-1(7-37), Val⁸Trp¹⁶Glu²²-GLP-1(7-37), Val⁸Leu¹⁶Glu²²-GLP-1(7-37), Val⁸Tyr¹⁸Glu²²-GLP-1(7-37), Val⁸Glu²²His³⁷-GLP-1(7-37), Val⁸Glu²²Ile³³-GLP-1(7-37), Val⁸Trp¹⁶Glu²²Val²⁵Ile³³-GLP-1(7-37), Val⁸Trp¹⁶Glu²²Ile³³-GLP-1(7-37), Val⁸Glu²²Val²⁵Ile³³-GLP-1(7-37), Val⁸Trp¹⁶Glu²²Val²⁵-GLP-1(7-37), and analogues thereof. In another embodiment said derivative of a GLP-1 analogue is Arg³⁴, Lys²⁶(Nᵋ-(γ-Glu(N^α-hexadecanoyl)))-GLP-1(7-37).

Methods for the preparation of GLP-1, analogues thereof as well as GLP-1 derivatives can be found in e.g. WO 99/43706, WO 00/55119, WO 00/34331 and WO 03/18516.

In another embodiment said solution or suspension of the bulk peptide product is subjected to treatment at a pH of 9.5, and the pH of said pharmaceutical composition is 7.4.

In another embodiment the glucagon-like peptide is a GLP-1 peptide and the pharmaceutical composition or a reconstituted composition thereof has a glucacon-like peptide concentration from 0.1 mg/mL to 50 mg/mL, from 0.1 mg/mL to 25 mg/mL, from 1 mg/mL to 25 mg/mL, from 1 mg/mL to 10 mg/mL, or from 3 mg/mL to 8 mg/mL.

In one embodiment the glucagon-like peptide is GLP-2, a GLP-2 analogue, a derivative of GLP-2 or a derivative of a GLP-2 analogue.

In another embodiment the derivative of GLP-2 or a derivative of a GLP-2 analogue has a lysine residue, such as one lysine, wherein a lipophilic substituent optionally via a spacer is attached to the epsilon amino group of said lysine.

Methods for the preparation of GLP-2, analogs thereof as well as GLP-2 derivatives can be found in e.g. WO 99/43361 and WO 00/55119.

In another embodiment the glucagon-like peptide is a GLP-2 peptide and the pharmaceutical composition or a reconstituted composition thereof has a glucagon-like peptide concentration from 0.1 mg/mL to 100 mg/mL, from 0.1 mg/mL to 25 mg/mL, or from 1 mg/mL to 25 mg/mL.

In one embodiment the glucagon-like peptide is exendin-4, an exendin-4 analogue, a derivative of exendin-4, or a derivative of an exendin-4 analogue.

In another embodiment the glucagon-like peptide is exendin-4. In another embodiment the glucagon-like peptide is a stable exendin-4. In another embodiment the glucagon-like peptide is a DPP-IV protected exendin-4. In another embodiment the glucagon-like peptide is an immunomodulated exendin-4. In another embodiment the glucagon-like peptide is ZP-10 ([Ser³⁸Lys³⁹]Exendin-4(1-39)LysLysLysLysLys-amide).

Methods for the preparation of exendin-4, analogues thereof as well as exendin-4 derivatives can be found in e.g. WO 99/43708, WO 00/41546 and WO 00/55119.

In another embodiment the glucagon-like peptide is an exendin-4 peptide and the pharmaceutical composition or a reconstituted composition thereof has a concentration of glucagon-like peptide from 5 μg/mL to 10 mg/mL, from 5 μg/mL to 5 mg/mL, from 5 μg/mL to 5 mg/mL, from 0.1 mg/mL to 3 mg/mL, or from 0.2 mg/mL to 1 mg/mL.

Buffers suitable for use in pharmaceutical compositions are known to those skilled in the art and include, but are not limited to, ortho-phosphate, TRIS, glycine, N-glycylglycine, citrate sodium acetate, sodium carbonate, glycylglycine, histidine, lysine, arginine, sodium phosphate, and sodium citrate or mixtures thereof. In one embodiment the pharmaceutical composition comprises a buffer which is Tris. In another embodiment the pharmaceutical composition comprises a buffer which is Bicine.

Preservatives for use in pharmaceutical compositions are known to those skilled in the art and include, but are not limited to, phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof.

In one embodiment the pharmaceutical composition comprises an isotonicity agent.

In another embodiment the pharmaceutical composition comprises an isotonicity agent which is sodium chloride, xylitol, mannitol, sorbitol, glycerol, glucose, maltose, sucrose, L-glycine, L-histidine, arginine, lysine, isoleucine, aspartic acid, tryptophan, threonine, dimethyl sulphone, polyethyleneglycol, propylene glycol or mixtures thereof.

In another embodiment of the present invention the pharmaceutical composition further comprises a stabilizer.

In a further embodiment of the invention the formulation further comprises a stabilizer selected from the group of high molecular weight polymers or low molecular compounds.

In a further embodiment of the invention the stabilizer is selected from polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine and mixtures thereof. Each one of these specific stabilizers constitutes an alternative embodiment of the invention. In a preferred embodiment of the invention the stabilizer is selected from the group consisting of L-histidine, imidazole and arginine.

In another embodiment of the present invention the stabilizer is selected from the group consisting of PEG 3350, polyvinylalcohol, polyvinylpyrrolidone, carboxy-methylcellulose, sodium chloride, L-glycine, L-histidine, imidazole, L-arginine, L-lysine, L-isoleucine, L-aspartic acid, Ltryptophan, L-threonine and mixtures thereof.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. Each one of these specific chelating agents constitutes an alternative embodiment of the invention. In another embodiment of the present invention the pharmaceutical composition further comprises a surfactant. In a further embodiment of the invention the surfactant is selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the postively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment of the invention.

The use of excipients such as preservatives, isotonic agents and surfactants in pharmaceutical compositions is well-known to the skilled person. For convenience reference is made to Remington: *The Science and Practice of Pharmacy,* $19^{th}$ edition, 1995.

In a further aspect the present invention relates to a pharmaceutical composition which comprises a glucagon-like peptide, a pharmaceutically acceptable buffer and a pharmaceutically acceptable preservative, characterized in that said pharmaceutical composition is prepared by a method according to the present invention.

In a further aspect the present invention relates to a pharmaceutical composition having a pH between about 7.2 to about 7.8, said composition comprising a glucagon-like peptide and at least one pharmaceutically acceptable excipient, wherein said composition is shelf stable as measured by a less than two fold increase of fluorescence in a Thioflavin T test of the glucagon-like peptide contained in said composition after storage of the composition for one month at 37° C.

In a further aspect the present invention relates to a pharmaceutical composition which comprises a peptide, a pharmaceutically acceptable buffer and a pharmaceutically acceptable preservative, characterized in that said pharmaceutical composition is prepared by a method according to the present invention.

In a further aspect the present invention relates to a method for treatment of hyperglycemia comprising parenteral administration of an effective amount of the pharmaceutical composition according to the present invention.

The parent glucagon-like peptide can be produced by peptide synthesis, e.g. solid phase peptide synthesis using t-Boc or F-Moc chemistry or other well established techniques. The parent glucagon-like peptide can also be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question. The DNA sequence encoding the parent peptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, Molecular Cloning: A Laboratory Manual, Cold Spring Harbor Laboratory Press, New York, 1989). The DNA sequence encoding the peptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. The DNA sequence may also be prepared by polymerase chain reaction using specific primers, for instance as described in U.S. Pat. No. 4,683,202 or Saiki et al., Science 239 (1988), 487-491. The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

In the following "Compound 1" is intended to mean: $Arg^{34}$, $Lys^{26}$ ($N^{\epsilon}$-($\gamma$-Glu($N^{\alpha}$-hexadecanoyl)))GLP-1(7-37).

Before freeze drying the solution or suspension of the peptide it has been adjusted to the aimed pH. After freeze drying pharmaceutical formulations were prepared according to General procedure 1 and 2.

General Procedure 1

Preservative, isotonic agent and buffer were dissolved in water and pH adjusted to 7.4. Hereafter the freeze dried peptide was dissolved while stirring slowly. The pH was adjusted to 7.4 using Sodium Hydroxide and/or Hydrochloric Acid. Finally, the formulation was filtered through a 0.22 μm filter.

General Procedure 2

Preservative, isotonic agent and buffer were dissolved in water and pH adjusted to 7.4. The peptide was dissolved in water while stirring slowly. The two solutions were mixed and pH adjusted to 7.4 using Sodium Hydroxide and/or Hydrochloric acid. Finally, the formulation was filtered through a 0.22 μm filter.

Another way to make a stable pharmaceutical formulation is to raise pH above neutral pH (>8) in the solution containing the drug substance. The pharmaceutical formulation is prepared as described in general procedure 3.

General Procedure 3

Preservative, isotonic agent and buffer were dissolved in water and pH adjusted to 7.4 or lower. Compound 1 was dissolved in water while stirring slowly and pH is adjusted to 11.5 by the addition of Sodium Hydroxide. After approx. 5 min the two solutions were mixed and pH adjusted to 7.4 using Sodium Hydroxide and/or Hydrochloric acid. Finally, the formulation was filtered through a 0.22 μm filter.

Physical stability of the formulations is evaluated by means of the Thioflavin T-test. The physical stability of the different formulations is characterized by their tendency to form fibrils. A method to determine the presence of fibrils is the Thioflavin T-test. The histological thiazole dye Thioflavin T (ThT) is used as an indicator of amyloid fibril formation. The method is based on the fluorescent characteristics of ThT. In the presence of amyloid fibrils, the fluorescence of ThT exhibits an excitation maximum at 450 nm and enhanced emission at 482 nm. The ThT fluorescence intensity has been shown to be linear with the increase in amyloid fibril concentration. The physical stability of the formulations is evaluated by the ThT-test after storage of the formulation is top filled glass cartridges for various time periods.

Results from Pharmaceutical Formulation Manufactured with Drug Substance Adjusted to a pH Above Neutral pH (>8) Before Freeze Drying The results from ThT-test at start (t=0) and after 1 months storage at 37° C. can be seen in Table 1.

TABLE 1

Results from ThT-test (fluorescence units) after 1 week or 1 month of accelerated stability testing.

| pH of Compound 1 before freeze drying | Concentration of Compound 1 in pharmaceutical formulation | pH of pharmaceutical formulation | Fluorescence units after storage at 37° C. | | |
|---|---|---|---|---|---|
| | | | T = 0 week | T = 1 week | T = 1 month |
| 8.0 | 3 mg/ml | 7.4 | 6 | Not determined | 28 |
| 9.5 | 3 mg/ml | 7.4 | 6 | Not determined | 7 |
| 11.5 | 3 mg/ml | 7.4 | 6 | Not determined | 7 |
| 8.0 | 6.25 mg/ml | 7.4 | 13 | 20 | 37 |

TABLE 1-continued

Results from ThT-test (fluorescence units) after 1 week or 1 month of accelerated stability testing.

| pH of Compound 1 before freeze drying | Concentration of Compound 1 in pharmaceutical formulation | pH of pharmaceutical formulation | Fluorescence units after storage at 37° C. | | |
|---|---|---|---|---|---|
| | | | T = 0 week | T = 1 week | T = 1 month |
| 9.5 | 6.25 mg/ml | 7.4 | 14 | 13 | 13 |
| 11.5 | 6.25 mg/ml | 7.4 | 14 | 13 | 14 |

It is seen that the pharmaceutical formulations manufactured with Compound 1 adjusted to pH 9.5 and 11.5 before freeze drying is more physically stable after 1 week and 1 months storage at 37° C. (as no increase in ThT is seen) compared to the pharmaceutical formulation manufactured with Compound 1 adjusted to pH 8.0 before freeze drying (where an increase in ThT is seen).

Results of Pharmaceutical Formulation Manufactured by Raising pH Above Neutral pH (>8) in the Solution Containing the Drug Substance.

TABLE 2

Results from ThT-test (fluorescence units) after 1 month of accelerated stability testing.

| pH of solution containing the drug substance | Concentration of Compound 1 in pharmaceutical formulation | pH of pharmaceutical formulation | Fluorescence units after storage at 37° C. | | |
|---|---|---|---|---|---|
| | | | T = 0 week | T = 1 week | T = 1 month |
| 8.0 | 6.25 mg/ml | 7.4 | 14 | 20 | 41 |
| 11.5 | 6.25 mg/ml | 7.4 | 13 | 12 | 13 |

It is seen that the pharmaceutical formulation manufactured by raising pH above neutral pH (>8) in the solution containing the drug substance is physically stable after 1 month at 37° C. (as no increase in ThT is seen) compared to the pharmaceutical formulation manufactured without the increase of pH to above neutral pH (>8).

---

The invention claimed is:

1. A pharmaceutical composition which comprises a glucagon-like peptide, wherein said pharmaceutical composition is prepared with a method for increasing the shelf-life of a pharmaceutical composition comprising a glucagon-like peptide, a pharmaceutically acceptable buffer and a pharmaceutically acceptable preservative, the method comprising preparing said pharmaceutical composition from a bulk glucagon-like peptide product which has been subjected to treatment at a pH in the range from 8.5 to 11.5 prior to freeze drying, and freeze drying the bulk glucagon-like peptide, wherein the pH of the pharmaceutical composition ranges from pH 7.0 to pH 8.5 and wherein the pharmaceutical composition is shelf stable as measured by a less than two fold increase of fluorescence in a Thioflavin T test of the glucagon-like peptide contained in said composition after storage of the composition for one month at 37° C.

2. A method for treatment of hyperglycemia, said method comprising parenterally administering to a patient in need of said treatment an effective amount of the pharmaceutical composition according to claim 1.

3. The pharmaceutical composition of claim 1, wherein the bulk glucagon-like peptide product which has been subjected to treatment at a pH in the range from 8.5 to 11.5 for a time period from about 10 minutes to about 12 hours at a temperature from about 5° C. to about 25° C.

4. The pharmaceutical composition of claim 1, wherein the bulk glucagon-like peptide product which has been subjected to treatment at a pH in the range from 8.5 to 11.5 for a time period from about 1 minute to about 30 minutes at a temperature from about 5° C. to about 25° C.

5. The pharmaceutical composition of claim 1, wherein the pH of the pharmaceutical composition is lower than the pH at which the solution or suspension of the bulk peptide has been subjected.

6. The pharmaceutical composition of claim 1, wherein the pharmaceutical composition is suitable for parenteral administration.

7. The pharmaceutical composition of claim 1, wherein the pH of the pharmaceutical composition ranges from pH 7.2 to pH 7.8.

8. The pharmaceutical composition of claim 1, wherein the glucagon-like peptide is selected from the group consisting of glucagon, a glucagon analogue, and derivatives thereof.

9. The pharmaceutical composition of claim 1, wherein the glucagon-like peptide is glucagon-like peptide 1 (GLP-1), a GLP-1 analogue, a derivative of GLP-1, or a derivative of a GLP-1 analogue.

10. The pharmaceutical composition of claim 9, wherein the GLP-1 analogue is selected from the group consisting of Gly$^8$-GLP-1(7-36)-amide, Gly$^8$-GLP-1(7-37), Val$^8$-GLP-1(7-36)-amide, Val$^8$-GLP-1(7-37), Val$^8$Asp$^{22}$-GLP-1(7-36)-amide, Val$^8$ Asp$^{22}$-GLP-1(7-37), Val$^8$Glu$^{22}$-GLP-1(7-36)-amide, Val$^8$Glu$^{22}$-GLP-1(7-37), Val$^8$Lys$^{22}$-GLP-1(7-36)-amide, Val$^8$Lys$^{22}$-GLP-1(7-37), Val$^8$Arg$^{22}$-GLP-1(7-36)-amide, Val$^8$Arg$^{22}$-GLP-1(7-37), Val$^8$His$^{22}$-GLP-1(7-36)-amide, Val$^8$His$^{22}$-GLP-1(7-37), Val$^8$Trp$^{19}$Glu$^{22}$-GLP-1(7-37), Val$^8$Glu$^{22}$Val$^{25}$-GLP-1(7-37), Val $^8$Tyr$^{16}$Glu$^{22}$-GLP-1(7-37), Val$^8$Trp$^{16}$Glu$^{22}$-GLP-1(7-37), Val$^8$Leu$^{16}$Glu$^{22}$-GLP-1(7-37), Val$^8$Tyr$^{18}$Glu$^{22}$-GLP-1(7-37), Val$^8$Glu$^{22}$His$^{37}$-GLP-1(7-37), Val$^8$Glu$^{22}$Ile$^{33}$-GLP-1(7-37), Val$^8$Trp$^{16}$Glu$^{22}$Val$^{25}$Ile$^{33}$-GLP-1(7-37), Val$^8$Trp$^{16}$Glu$^{22}$Ile$^{33}$-GLP-1(7-37), Val$^8$Glu$^{22}$Val$^{25}$Ile$^{33}$-GLP-1(7-37), Val$^8$Trp$^{16}$Glu$^{22}$Val$^{25}$-GLP-1(7-37), and analogues thereof.

11. The pharmaceutical composition of claim 9, wherein said derivative of a GLP-1 analogue is Arg$^{34}$, Lys$^{26}$(N$^\epsilon$-(γ-Glu(N$^\alpha$-hexadecanoyl)))-GLP-1(7-37).

12. The pharmaceutical composition of claim 11, wherein bulk glucagon-like peptide product has been subjected to treatment at a pH of about 9.7 and the pH of the pharmaceutical composition is about 8.1.

* * * * *